US005569753A

United States Patent [19]

Wigler et al.

[11] Patent Number: 5,569,753
[45] Date of Patent: Oct. 29, 1996

[54] CANCER DETECTION PROBES

[75] Inventors: Michael Wigler, Lloyd Harbor; Nikolai Lisitsyn, Cold Spring Harbor, both of N.Y.

[73] Assignee: Cold Spring Harbor Laboratory, Cold Spring Harbor, N.Y.

[21] Appl. No.: 360,096

[22] Filed: Dec. 20, 1994

[51] Int. Cl.⁶ ............................. C07H 21/04; C07H 19/00
[52] U.S. Cl. .................... 536/24.3; 536/22.1; 536/24.31; 536/24.33
[58] Field of Search ............................. 435/6; 536/24.3, 536/22.1, 23.1, 24.1, 24.31

[56] References Cited

PUBLICATIONS

Lisitsyn, et al., Comparative Genomic Analysis of Tumors: Detection of DNA Losses and Amplification (Jan. 1995) Proc. Natl. Acad. Sci. USA, vol. 92:151–155.

Chang, et al., Identification of Herpesvirus–Like DNA Sequences in AIDS–Associated Kaposi's Sarcoma (Dec. 1994) Science, vol. 266:1865–1869.

Cohen, Is a New Virus the Cause of KS? (Dec. 1994) Science, vol. 266:1803–1804.

Pool, Can Sound Drive Fusion in a Bubble? (Dec. 1994) Science, vol. 266:1804.

Altman, Apparent Virus May Be a Cause of Fatal Cancer in AIDS Patents (Dec. 1994) New York Times, pp. A1–A2.

Rosenberg, et al., RFLP Subtraction; A Method for Making Libraries of Polymorphic Markers (Jun. 1994) Proc. Natl. Acad. Sci., vol. 91:6113–6117.

Hubank, et al., Identifying Differences in mRNA Expression by Representational Difference Analysis of cDNA (1994) Nucleic Acids Research, vol. 22, No. 25:5640–5648.

Solomon, et al., Chromosome Aberrations and Cancer, (1991) Science, 254:1153.

Lasko, et al., Loss of Constitutional Heterozygosity in Human Cancer, (1991) Annu. Rev. Genet. 25:281–314.

Lisitsyn, et al., Cloning the Differences Between Two Complex Genomes, (1993) Science, 259:946–951.

Lisitsyn, et al., Direct Isolation of Polymorphic Markers Linked to a Trait By Genetically Directed Representational Difference Analysis, (1994) Nature Genetics 6:57–63.

Presti, Jr., et al., Histopathological, Cytogenetic, and Molecular Characterization of Renal Cortical Tumors, (1991) Cancer Research 51:1544–1552.

Schwab, et al., Amplification of Cellular Oncogenes: A Predictor of Clinical Outcome in Human Cancer, (1990) Genes, Chromosomes & Cancer 1:181–193.

*Primary Examiner*—W. Gary Jones
*Assistant Examiner*—Ethan Whisenant
*Attorney, Agent, or Firm*—Bertram I. Rowland

[57] ABSTRACT

Nucleic acid sequence probes are provided for the detection of lesions associated with neoplastic cells. The sequences can be used for identifying the locus associated with the lesion, for determining cancer susceptibility of cells, as well as categorizing and characterizing tumor cells for prognosis and therapy.

4 Claims, No Drawings

CANCER DETECTION PROBES

TECHNICAL FIELD

The field of this invention is the identification of lesions in neoplastic cells.

BACKGROUND

The etiology of neoplasia is an extremely complex one. A large number of genes have been found to be associated with normal cells being transformed into tumor cells. Genes that have been identified include genes which enhance cell proliferation and suppress cell proliferation. The present view is that it takes more than one mutation event to take a cell from the phenotype of the normal state to the phenotype of the tumor state.

It appears today that human tumors are genetically heterogeneous by the time of clinical presentation, even though they are rather monoclonal in origin. As the tumor progresses, there may be changes in the genome, such as deletions, insertions, substitutions, chromosomal arm exchanges, gene amplification, and the like. These changes may be associated with various characteristics of the cancer, which are important to the diagnosis and therapy of the patient. Information about the cancer, whether it is aggressive, metastatic, or responsive to a particular treatment as a result of particular genomic changes, can greatly aid in the choice of therapy of the patient. For example, more intensive treatment may be warranted for more aggressive cancers.

There is, therefore, substantial interest in identifying specific genetic differences which are associated with neoplastic cells. These differences provide the opportunity to identify groups of patients having analogous lesions, where the course of the cancer may be mapped. In this way, epidemiological data can be adduced as to the nature of the cancer, its response to different therapies, and probable outcomes.

Relevant Literature

Salomon et al. (1991) *Science* 254:1153 and Lasko et al. (1991) *Annu. Rev. Genet.* 25:281–314 describe genetic lesions found in tumors. Lisitsyn et al. (a) (1993) *Science* 259:946–951 describe a method called representational difference analysis (RDA) for analyzing differences between complex but related genomes. See also Lisitsyn et al. (b) (1993) *Nature Genetics*, 6:57–63. Presti et al. (1991) *Cancer Research* 51:1544–1552 report loss of at least portions of the Y chromosome in renal cell carcinoma cells. Schwab and Amler (1990) *Genes, Chromosomes and Cancer* 1:181–193 report the amplification of N-myc in neuroblastoma cells.

SUMMARY OF THE INVENTION

Nucleic acid probes for detecting cellular lesions associated with tumor cells are provided. The probes are associated with loss of heterozygosity ("LOH"), hemizygous loss, and homozygous loss. By combining the probe with genomic DNA of candidate cells and detecting the lesion, one can evaluate the cancer stage or provide a prognosis. The lesion can be detected by Southern blotting or other hybridization techniques, polymerase chain reaction, or other techniques.

DESCRIPTION OF THE SPECIFIC EMBODIMENTS

Compositions and methods are provided for detecting genomic lesions associated with cancer. Specific sequences are provided which may be used to detect the lesion in candidate cells, where cells having a normal phenotype may be evaluated for cancer susceptibility or cancer cells may be evaluated as to prognosis and therapy. The sequences may also be used to walk the genome, to identify other sequences at the locus of the specific sequence. (See, for example, Molecular Cloning: A Laboratory Manual, 2nd. ed., eds. Sambrook et al., CSHL Press, Cold Spring Harbor, N.Y., 1989, Sections 3.2, 3.9, 3.23, and 9.3) These other sequences at the locus provide additional probes, identify genes associated with the particular lesion and phenotype, and allow for the detection of specific mutations at the locus.

The specific sequences that can be used in the subject invention are set forth in Table 2. To obtain additional sequences at the locus of the subject sequences, human genomic fragments may be cloned in various sizes, generally ranging from about 10 kbp to 600 kbp or more. By identifying clones to which the probes base pair, one can then walk the probe to identify the sequences 3' and 5' of the probe. See Wahl et al. (1987) *P.N.A.S. U.S.A.* 84:2160; Triglia (1988) *Nucleic Acid Research* 16:8186; and Sambrook et al., infra. Depending upon the size of the cloned fragment, one can sequence the entire cloned fragment or further fragment the cloned fragment and sequence a smaller portion. With each extension of the subject sequences, one can then use the additional sequence to identify the next adjacent or contiguous sequence.

The sequences detected by walking the subject sequences and sequences uncovered this way can be screened in an analogous manner to the subject sequences to determine their usefulness as probes. The sequences can be used to screen normal genomes, as well as genomes from tumor cells. Where an unacceptable degree of binding to normal cells is uncovered or after screening a significant number of fresh tumor cells without significant observation of the same lesion, the sequence may be discarded and usually one will not proceed further in walking the DNA. This will be particularly true, where there is a high incidence of the lesion in normal cells. For example, some particular sequences may be found absent in tumors but have a high incidence of being absent in normal human DNA. We call these deletion or insertion polymorphisms. Generally, the lesion will be absent in 20 randomly selected normal cells, usually absent in 100 randomly selected normal cells, and absent in the normal cells of the source. The lesion is desirably absent in at least a statistically significant proportion of the normal population to provide a cancer diagnostic, but may be present in the normal population, where it is directed to prognosis of an existing tumor, recurrence or remission.

The loci of the subject invention identified by the subject probes will generally be not more than about 300 kbp, usually not more than about 100 kbp and may not exceed about 10 kbp. The probes employed in this invention as obtained from the specified loci will generally be at least about 18 bp, more usually at least about 30 bp and may be 1 kbp or more, usually not exceeding about 40 kbp. While the probes may be either DNA or RNA, as a practical matter the probes will normally entail DNA.

The loci can be present on both autosomal chromosomes or sex chromosomes. For particular types of cancer, there will normally be an association between the type of cancer and the particular lesion. In addition, particular lesions can provide for susceptibility of cells to cancer formation, the aggressiveness of the cancer, particularly as to rate of proliferation and metastatic capability, as well as the response of the cancer cells to particular forms of therapy. The subject loci are associated with carcinomas, as associated with cells from the kidney, colon, esophagus, lung, skin, and brain.

The probes of this invention are further characterized by detecting lesions which are present in neoplastic cells, but not present in normal cells of the same patient, as well as normal cells from other individuals. Frequently, the same lesion may be found in human tumor cell lines and human cells from the same cellular type.

For use in detection of lesions, the probes may be modified by various labels, which will allow for their detection. The labels may be directly detectable, such as fluorescers, enzymes, radioisotopes, particles, and the like. Alternatively, the labels may be indirectly detectable by binding to another molecule which provides for the direct detection. Thus, one may have various ligands which have a complementary pair binding member, where the complementary binding pair member is labeled. Illustrative ligands include biotin, which binds to strepavidin, digoxigenin, which binds to an antibody to digoxigenin, other haptens, and their complementary antibodies, and the like. Other labels may also find application, such as labels providing for chemiluminescence, and channeling, where the probe brings two moieties together, which only interact to provide a signal when in spacial proximity.

The subject probes can be employed in a variety of methodologies to detect the presence of the particular lesion. For example, Southern blotting may be employed with genomic fragments. Alternatively, one may use the polymerase chain reaction, where the subject sequence or portion thereof may be one primer, or distal portions of the subject sequence may be used as two primers. Where the sequence is used as a single primer, a second primer can be employed where the sequence is chosen to have a high likelihood of being present within about 2 kbp of the subject sequence.

Other techniques may involve having a probe with a convenient restriction site, where one end of the probe is tethered to a particle and the other end is labeled with a detectable label, combining the particle bound probes with the sample, followed by separation of the particles and washing away of non-specific DNA. The amount of label in the medium can be detected, followed by addition of the restriction enzyme, separating the particles free of non-bound DNA and detecting the label again. A significant reduction in the amount of label is indicative of the presence of the sequence in the sample. Additionally, one may employ magnetic particles which allow for separation of DNA binding to the subject probe, where the DNA binding to the subject probe may then be detected in a variety of ways, which will be discussed subsequently.

One may also use gel electrophoresis, where it is found that the locus provides for a restriction fragment length polymorphism that is absent in tumor cells but present in normal cells, or the like. Other techniques may include triplex formation and detection using RecA. For further discussion of techniques for detecting specific DNA sequences, see *Molecular Cloning: A Laboratory Manual,* Sambrook et al., eds., Cold Spring Harbor Laboratory, Cold Spring Harbor, N.Y., 1988.

DNA from cells may be obtained by any convenient means, for the most part the techniques are now well established. Cells may be lysed, the DNA precipitated, isolated, redispersed, washed and then fragmented, usually employing restriction enzymes. The particular manner in which the DNA is isolated is not critical to this invention. It is not even necessary to isolate DNA, since fluorescence in-situ-hybridization can be used directly on tissue sections.

(See, for example, Matsumura, et al. (1992) Cancer Res. 52:3474–3477.) The significant factor is that one can detect the presence of the lesion in tumor cells, where the presence of the lesion is indicative of susceptibility, prognosis or therapy.

The probes may be used at various degrees of stringency, depending upon the size of the probe, its composition, the degree of polymorphism anticipated at the homologous site, similarity of the sequence at other sequences, and the like. Relatively mild stringencies may be employed, from about 0.1–1×SSC, 0.1–1% SDS, at temperatures in the range of about 50° to 80° C., or the equivalent thereof.

Kits can be provided where two or more probes are provided from the loci of the subject sequences, which are labeled as previously described. In this manner, the kits can be used for screening human cells as described above.

The following examples are offered by way of illustration and not by way of limitation.

EXPERIMENTAL

Materials and Methods

Cell lines and DNA samples. Renal cell carcinoma cell lines UOK112, UOK114, UOK124, UOK132, UOK108, UOK111, UOK127, UOK146, UOK154 and normal DNAs from the same patients were obtained as described (Angland et al. (1992) *Cancer Research* 52:348–3565). Colorectal cancer cell lines VACO 429, VACO 441, VACO 432, VACO 456, VACO 476, RBX and matched normal DNA were established according to Willson et al. (1987) J. Cancer Research 47:2704–2713. Cell line NCI H1770 (small cell lung carcinoma) and EBV-immortalized lymphocytes from the same patient were supplied by J. D. Minna (Southwestern Medical School, Dallas). DNAs from the melanoma tumor cell lines AH-Mel, FF-Mel, BD-Mel and DX-Mel and matched EBV-immortalized cells were the gift of A. Houghton (Memorial Sloan-Kettering Cancer Center, New York). Cell lines A382 (astrocytoma), VM-CUB-2 (bladder cancer), SK-LC-6, SK-LC-13, SK-LC-14, SK-LC-17, SHP-77 (lung cancers), and WILTU-1 (Wilm's tumor) were from the J. Fogh collection (Memorial Sloan-Kettering Cancer Center). All other tumor cell lines were obtained from the ATCC. DNAs NA04844, NA1102 and human/rodent somatic cell hybrid mapping panel #2 were purchased from NIGMS Human Genetic Mutant Cell Repository (Camden, N.J.).

The "standard blotting panel" included Bgl II digests of DNAs from tumor cell lines BD-Mel, AH-Mel (melanomas), T24, VM-CUB-2 (bladder cancers), SK-BR-3, MCF7 (breast cancers), HT-29, SW480, SW620 (colon cancers), A-172, U-118 MG (glioblastomas), A-382 (astrocytoma), NCI H1770, Sk-Lu-1, SK-LC-6, SK-LC-13, SK-LC-14, SK-LC-17, SHP-77 (lung cancers), SK-N-MC, SK-N-SH, IMR-5, (neuroblastomas), G-401 (Wilm's tumor) and normal control DNA NA04844. Allele frequency blots were prepared using Bgl II digests of human DNAs from various races (allele frequency kit, BIOS Laboratories, New Haven). The standard PCR panel included DNAs from tumor cell lines BT-20, MCF7, SK-BR-3, T-47D, BT-549, MDA-MBA-435S, MDA-MB-436, MDA-MB-231, MDA-MD-453, MDA-MB-468 (breast cancers); UOK124, OUK161, UOK114, UOK112, UOK132, UOK154, UOK127, UOK111, UOK146, UOK108 (renal cell carcinomas); LS180, SW403, SW480, HT29, LoVo, DLD-1, Caco-2, HCT-15, VACO 429, VACO 441 (colon cancers); FF-Mel, BD-Mel, AH-Mel, DX-Mel, HT-144, SK-Mel-2, SK-Mel-3, G-361, WM266-4, Malme-3M (melanomas); T24, VM-CUB-2, UM-UC-3, J82, SCaBER, HT-1376 RT-4, HT-1197 (bladder cancers); and normal control DNA NA04844. Tumor and normal cells were grown as recommended and DNAs were purified using cell culture DNA Maxi kit (Qiagen Inc.). Diploid and aneuploid nuclei were separated by flow cytometry from a biopsy of a patient with Barrett's esophagus (Blount et al. (1991) *Cancer Research* 51:5482–5486) and 100 ng of DNA from each diploid and aneuploid fraction ($10^5$ nuclei each) were purified after lysis in SDS-proteinase K buffer, phenol-chloroform extraction and ethanol precipitation.

Representational difference analysis. The RDA procedure was performed as previously described (See Lisitsyn et al. [1993a and b]) using Bgl II restriction endonuclease (New England Biolabs). When DNAs from flow sorted material were used, 100 ng of each driver and tester was digested with Bgl II and ligated to adapters in a volume of 30 µl. After ligation, 10 µg of tRNA (5 mg/ml), 90 µl of TE buffer, 30 µl of 10M ammonium acetate and 380 µl of ethanol were added. The DNA pellet was recovered by centrifugation and dissolved in 10 µl of TE buffer. 40 µl of the DNA ligate was PCR amplified for 20 cycles in a volume of 400 µl taking two tubes for preparation of driver and two tubes for preparation of tester representation. To get sufficient quantity of DNA, 40 µl of the product of the first PCR was directly added to each of 12 tubes used for preparation of driver representation and reamplified for 5 cycles in a volume of 400 µl under standard conditions. The subsequent PCR amplification of tester representation was made in the same way, taking 2 tubes. All subsequent steps were performed as described by Lisitsyn et al.,(a) 1993. RDA difference products were digested with Bgl II, ligated to Bam HI-digested and dephosphorylated pBluescript SK(-) (Strategene), and transformed into *E. coli* XL-Blue competent cells according to the supplier's recommendations.

Characterization and mapping of RDA probes. Plasmid inserts were PCR amplified and those with distinct sizes were selected, purified, and hybridized to Southern blots containing Bgl II representations of driver, tester, one normal male and one normal female DNA prepared as described (Lisitsyn et al., (b) 1993). Sequences present in tester but not in driver representations were hybridized to Southern blots containing Bgl II digested DNAs from the standard blotting panel and to allels frequency blots. These blots were washed two times, 30 min. each, in 0.1×SSC, 0.5% SDS at 68° C. Selected plasmid inserts were sequenced on both strands, using Sequenase T7 DNA polymerass reagent kit (United States Biochemical) as recommended by the supplier. Oligonucleotides derived from the sequences were synthesized, and used for screening the standard PCR panel of DNAs. 250 ng of template was taken per each 100 µl PCR reaction containing 1 µM primers. Amplification was made for 32 cycles. Negative reactions were independently repeated two times.

Mapping of probes on human chromosomes was performed by PCR using 250 ng of DNAs from NIGMS human/rodent somatic cell hybrid mapping panel #2 as templates under the same conditions (Lisitsyn et al., (b) 1993). To sublocalize probes on chromosome 3, DNA from hybrid clone GM 11102 retaining the der(3) t(3;16) (q13.2;q13) chromosome was used (NIGMS Human Genetic Mutant Cell Repository). Fluorescent in situ hybridization was performed as described (Barker and Schwab (1983) *Gene and Chromosome Analysis*, Vol. 2, 129–154).

Results

Tumor DNA as driver. We performed RDA on sixteen individual pairs of tumor DNAs (used as driver) and matched normal DNAs (used as tester) derived from the same patient, as otherwise cloning of polymorphic differences between different individuals predominates. In all cases, we used Bgl II as the restriction endonuclease to prepare representations. Pure tumor DNAs were isolated from fifteen tumor cell lines (including nine RCC and 6 colon cancer cell lines), and normal DNA was derived from unaffected blood or tissue but not from EBV- immortalized cell lines. In one case we used a fluorescent activated cell sorter to fractionate nuclei from an esophageal cancer biopsy into aneuploid and diploid fractions that were used for preparation of driver and tester DNA, respectively.

In each application of RDA, 2–13 difference products were observed and cloned into plasmids. Plasmid clones were picked at random and inserts of different sizes were analyzed by hybridization to blots containing representations from the normal (tester) and tumor (driver) DNAs, as well as Bgl II representations of normal male and female DNAs. The "informative" probes, that were hybridizing to one band on a blot, and were absent in the driver representation, were taken for further analysis, except for those that derived from the Y chromosome (loss of the Y chromosome information was frequently observed in renal cell carcinomas). In the search for clones detecting single copy sequences which are frequently lost in tumors, informative probes were hybridized to blots containing Bgl II digested DNAs from a standard blotting panel of human tumor cell lines. Those probes that were commonly polymorphic at Bgl II sites were presumed to have arisen by loss of heterozygosity, and were not further studied unless they did not detect any bands in at least one tumor DNA on a blot. Probes of this type, as well as the remaining nonpolymorphic single copy probes, were sequenced, and oligonucleotides derived from the sequence were synthesized to be used for PCR screening of total genomic DNA from tester, driver, and panels of human tumor cell lines. All probes absent in two or more DNA samples from standard PCR panel were hybridized to allele frequency blots containing Bgl II digests of human DNAs from various races. This way we were able to find two probes which did not hybridize to any sequences in several normal human DNAs. We thus presume that these two probes actually detect hemizygous loss of a deletion polymorphism (see Table 1, footnote c). Tables 1 and 2 summarize all of our results obtained using tumor DNA as driver.

TABLE 1

|  | Selected for initial characterization | Found to be informative[a] |
|---|---|---|
| A. Renal Cell Carinoma: | | |
| 1. UOK 112 (male) | 13[b] | 13 (0/13/0) |
| 2. UOK 114 (female) | 12[b] | 4 (3/0/1) |
| 3. UOK 124 (female) | 12[b] | 4 (4/0/0) |
| 4. UOK 132 (male) | 10[b] | 9 (3/6/0) |
| 5. UOK 108 (female) | 2 | 2 (2/0/0) |
| 6. UOK 111 (female) | 5 | 5 (5/0/0) |
| 7. UOK 127 (male) | 3 | 3 (2/1[c]/0) |
| 8. UOK 146 (female) | 3 | 3 (1/1[c]/1) |
| 9. UOK 154 (female) | 5 | 1 (1/0/0) |
| B. Colon Cancer: | | |
| 10. VACO 429 (male) | 2 | 1 (0/0/1) |
| 11. VACO 441 (female) | 3 | 3 (1/0/2) |
| 12. VACO 432 (male) | 2 | 1 (1/0/0) |
| 13. VACO 456 (female) | 2 | 1 (1/0/0) |
| 14. VACO 576 (female) | 2 | 2 (2/0/0) |

TABLE 1-continued

| | Selected for initial characterization | Found to be informative[a] |
|---|---|---|
| 15. RBX (male) | 2 | 1 (1/0/0) |
| C. Barrett's Esophagus: | | |
| 16. BE 758 (male) (FACS sorted nuclei) | 5 | 5 (0/4/1[d]) |
| Total: | 83 | 58 (27/25/6) |

[a]Entries are a (b, c, d), were a is the total number of probes detecting DNA loss in tumors, judged to be: b - loss-of-heterozygosity, c - hemizygous loss, d - presumably homozygous loss. All but two probes judged to detect hemizygous loss were derived from the Y-chromosome. The difference between quantities of initially selected probes (83) and informative probes (58) was due to the presence of the repeat sequences (9 cases), nonhuman DNA contaminating tester (5 cases) and single copy sequences present in both tester and driver DNAs (11 cases).
[b]The difference products after two rounds of hybridization/selection were cloned; in all the rest of the experiments cloning was performed after three rounds.
[c]Probes 127-1 and 146-1 were found to be deletion polymorphisms, absent on both autosomes of 7 out of 35 and 3 out of 35 of normal humans, respectively.
[d]This result is presumed, but was not confirmed because of the small amount of sorted tumor nuclei available.

selection was found to be absent in the Bgl II representation of the tumor DNA. It was further analyzed by Southern blotting and PCR, indicating its frequent homozygous loss in many tumor cell lines. Subsequent PCR analysis of driver and tester DNAs indicated that UOK146–8 in fact detected loss of a small allele of a rare Bgl II polymorphism in the cell line UOK146, and was present in difference product due to loss of heterozygosity rather than homozygous loss in the original tumor. Probe UOK146-8 represents one of three probes detecting apparent homozygous loss in at least one tumor source, but isolated by virtue of loss of heterozygosity in the original tumor (see Table 2).

All probes that detected homozygous loss in at least one tumor cell line were mapped to human chromosomes using a panel of monochromosomal human/rodent somatic cell hybrids (see above). In two cases, an additional human/rodent hybrid was used to resolve location to 3p or 3q (see Table 2).

The subject probes provide means for identifying additional probes at the locus of the subject probes, for detecting susceptibility of cells to neoplasia, and for categorizing tumors in relation to prognosis and therapy. The probes were found by using RDA, which is described in application Ser.

TABLE 2

| Probe | Chrom. location | Cell lines with homozygous loss[a,b,c] | Sequences of primers used for PCR | Length of PCR product |
|---|---|---|---|---|
| UOK114-18 (SEQ ID NO 1) | 3p | 1/74 | CATTTCTTTAGGGTTCATTGTTGGAGC | 293 bp |
| (SEQ ID NO 2) | | | GAGCCCAGCCAGCAGTCCCACC | |
| UOK146-4 (SEQ ID NO 3) | 11 | 1/113 | CCATGCTGCCTCCGTTGACACTCA | 283 bp |
| (SEQ ID NO 4) | | | TGGCAACAATATCCATCCCTTTCCTG | |
| UOK124-6[d] (SEQ ID NO 5) | 2 | 2/113 | GTCTTCTCTCCCTCTTTCCCTCCC | 319 bp |
| (SEQ ID NO 6) | | | TGGCAGTAGAAGAGGAAAGATGTGTG | |
| UOK146-8[d] (SEQ ID NO 7) | 9 | 13/113 | TGTGCTCCCAGTCCTGCAGTCATC | 261 bp |
| (SEQ ID NO 8) | | | AGGGAACTCTGATGGTAGACTGGTC | |
| UOK132-12[d] (SEQ ID NO 9) | 9 | 6/86 | GCCCCTCTAAAAGATAAGGTCTTGGT | 272 bp |
| (SEQ ID NO 10) | | | GATCTGAGCCCCTGGAAGAAGTTAG | |
| VACO 429-6 (SEQ ID NO 11) | 20 | 1/86 | GGGAACAGTTCTCTTACAGCCACAC | 351 bp |
| (SEQ ID NO 12) | | | ACAGAGGTGACAACAAGGTCAGTGG | |
| VACO 441-1 (SEQ ID NO 13) | 18 | 1/86 | CCAGCTGTGTCCTCTCAGCAACAG | 268 bp |
| (SEQ ID NO 14) | | | ACATGATGCTGGCCTAGGTGAACTG | |
| VACO 441-9 (SEQ ID NO 15) | 18 | 1/86 | TCTAGGAACTGCCAGTGAGTGCTTG | 244 bp |
| (SEQ ID NO 16) | | | GTACTAACCAAGGAGCTGGTGACAC | |
| BE758-6 (SEQ ID NO 17) | 3p | 6/86 | GCTAAGCCTGGGGGAGTTGCTGAC | 315 bp |
| (SEQ ID NO 18) | | | GATTACTAAGGCTTTGAAAGCTGGCC | |

[a]The numbers show the ratio of the number of cell lines with apparent homozygous loss to the total number of analyzed cell lines. The primary determination was by PCR.
[b]The losses were detected in the following cell lines: probe UOK114-18 in UOK114[c]; probe UOK146-4 in UOK146; probe UOK124-6 in UOK141 and VM-CUB-2; probe UOK146-8 in UOK108, UOK122LN, UOK162, AH-Mel, Malme-3M, UM-UC-3, RT-4, MDA-MB-231, A-382, U-118 MG, A-172, SK-LU-1, and SK- LC-14; probe 132-12 in AH-Mel[c], FF-Mel[c], MDA-MB-231, A-382, U-118 MG, and A-172; probe VACO 429-6 in VACO 429; probes VACO 441-1 and VACO 441-9 in VACO 441, probe BE758-6 in LS180[c], HT-29[c], LoVo[c], MDA-MB-436[c], and VM-CUB-2[c]. See Materials and Methods for origins of cell lines.
[c]PCR data was additionally confirmed by genomic Southern blotting for the indicated cell lines.
[d]The probe was found to detect LOH in the initial normal/tumor DNA pair.

Illustrative of the experience with the different probes, RDA was performed using DNA from the renal cell carcinoma cell line UOK146 as driver. One of the probes (UOK146–8) cloned from the third round of hybridization/ Nos. 07/974,447 and 08/149,199, filed Nov. 12, 1992 and Nov. 9, 1993, respectively.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A DNA probe for detecting genomic lesions associated with cancer, said probe comprising:
   (a) a DNA sequence of 18 to 1000 bp selected from the group consisting of SEQ ID NO: 1, SEQ ID NO: 2, SEQ ID NO: 3, SEQ ID NO: 4 SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or the fully complementary sequence thereof, or
   (b) a labeled DNA sequence of 18 to 1000 bp selected from the group consisting of SEQ ID NO: 1, SEQ ID NO: 2, SEQ ID NO: 3, SEQ ID NO: 4 SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or the labelled fully complementary sequence thereof, wherein said label is capable of being detected.

2. A DNA according to claim 1, wherein said label is a radioisotope, a hapten, an enzyme, a fluorescer, chemiluminescer, or particle.

3. A labeled DNA probe for detecting genomic lesions associated with cancer, said probe comprising a sequence selected from the group consisting of (SEQ ID NO:01), (SEQ ID NO:02), (SEQ ID NO:03), (SEQ ID NO:04), (SEQ ID NO:05), (SEQ ID NO:06), (SEQ ID NO:07), (SEQ ID NO:08), (SEQ ID NO:09), (SEQ ID NO:10), (SEQ ID NO:11), (SEQ ID NO:12), (SEQ ID NO:13), (SEQ ID NO:14), (SEQ ID NO:15), (SEQ ID NO:16), (SEQ ID NO:17) and (SEQ ID NO:18).

4. A kit for detecting genomic lesions associated with cancer comprising at least two DNA probes according to claim 1.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GAGCCCAGCC AGCAGTCCCA CC        22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GAGCCCAGCC AGCAGTCCCA CC        22

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCATGCTGCC TCCGTTGACA CTCA        24

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TGGCAACAAT ATCCATCCCT TTCCTG        26

( 2 ) INFORMATION FOR SEQ ID NO:5:

( i ) SEQUENCE CHARACTERISTICS:
        ( A ) LENGTH: 24 base pairs
        ( B ) TYPE: nucleic acid (C) STRANDEDNESS: single
(D) TOPOLOGY: linear (i i) MOLECULE TYPE: cDNA (x i) SEQUENCE DESCRIPTION: SEQ ID NO:5:

GTCTTCTCTC CCTCTTTCCC TCCC                    24

(2) INFORMATION FOR SEQ ID NO:6:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:6:

TGGCAGTAGA AGAGGAAAGA TGTGTG                  26

(2) INFORMATION FOR SEQ ID NO:7:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:7:

TGTGCTCCCA GTCCTGCAGT CATC                    24

(2) INFORMATION FOR SEQ ID NO:8:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:8:

AGGGAACTCT GATGGTAGAC TGGTC                   25

(2) INFORMATION FOR SEQ ID NO:9:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:9:

GCCCCTCTAA AAGATAAGGT CTTGGT                  26

(2) INFORMATION FOR SEQ ID NO:10:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: cDNA ( x i ) SEQUENCE DESCRIPTION: SEQ ID NO:10:

GATCTGAGCC CCTGGAAGAA GTTAG   25

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGGAACAGTT CTCTTACAGC CACAC   25

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

ACAGAGGTGA CAACAAGGTC AGTGG   25

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CCAGCTGTGT CCTCTCAGCA ACAG   24

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

ACATGATGCT GGCCTAGGTG AACTG   25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TCTAGGAACT GCCAGTGAGT GCTTG   25

(2) INFORMATION FOR SEQ ID NO:16:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

GTACTAACCA AGGAGCTGGT GACAC 25

(2) INFORMATION FOR SEQ ID NO:17:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

GCTAAGCCTG GGGGAGTTGC TGAC 24

(2) INFORMATION FOR SEQ ID NO:18:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

GATTACTAAG GCTTTGAAAG CTGGCC 26